United States Patent [19]

Eisele

[11] Patent Number: 4,852,565
[45] Date of Patent: Aug. 1, 1989

[54] FENESTRATED TRACHEOSTOMY TUBE

[75] Inventor: Robert F. Eisele, Laguna Niguel, Calif.

[73] Assignee: Shiley Inc., Irvine, Calif.

[21] Appl. No.: 171,708

[22] Filed: Mar. 22, 1988

[51] Int. Cl.⁴ ............................................ A61M 16/00
[52] U.S. Cl. ........................... 128/207.14; 128/200.26; 128/204.18; 128/911
[58] Field of Search ....................... 128/200.26, 204.18, 128/207.14, 207.15, 911, 912, 205.19, 202.27, 202.28, 202.29, 206.29, 207.16, 207.17, 772, 348.1

[56] References Cited

U.S. PATENT DOCUMENTS

| | | | |
|---|---|---|---|
| 3,659,612 | 5/1972 | Shiley et al. | 128/207.15 |
| 3,693,624 | 9/1972 | Shiley et al. | 128/207.15 |
| 4,315,505 | 2/1982 | Crandall et al. | 128/200.26 |
| 4,332,245 | 6/1982 | Boone, Sr. | 128/207.17 |
| 4,612,927 | 9/1986 | Krüger | 128/200.26 |
| 4,637,389 | 1/1987 | Heyden | 128/207.15 |
| 4,688,568 | 8/1987 | Trass et al. | 128/207.15 |

Primary Examiner—Edgar S. Burr
Assistant Examiner—Kimberly L. Asher
Attorney, Agent, or Firm—Peter C. Richardson; Larry C. Akers; Roger C. Turner

[57] ABSTRACT

The present invention discloses an improved fenestrated tracheostomy tube which includes a tubular outer cannula which has a distal end for insertion within the trachea and a proximal end which remains outside of the patient. The outer cannula has a generally circular longitudinal radius of curvature and has an upper wall portion with a longitudinal center along its uppermost surface. The tube includes a disposable inner cannula having a distal end and a proximal end which is adapted to fit closely within and to be removably inserted into the outer cannula. The outer cannula has a plurality of slotted fenestrations through the upper wall portion arranged so that each fenestration is slightly spaced from the longitudinal center and forms an acute angle away from the longitudinal center in the direction of the distal end of the outer cannula. With the foregoing fenestration arrangement, the inner cannula is readily inserted into the outer cannula free from interference with the fenestrations.

5 Claims, 2 Drawing Sheets

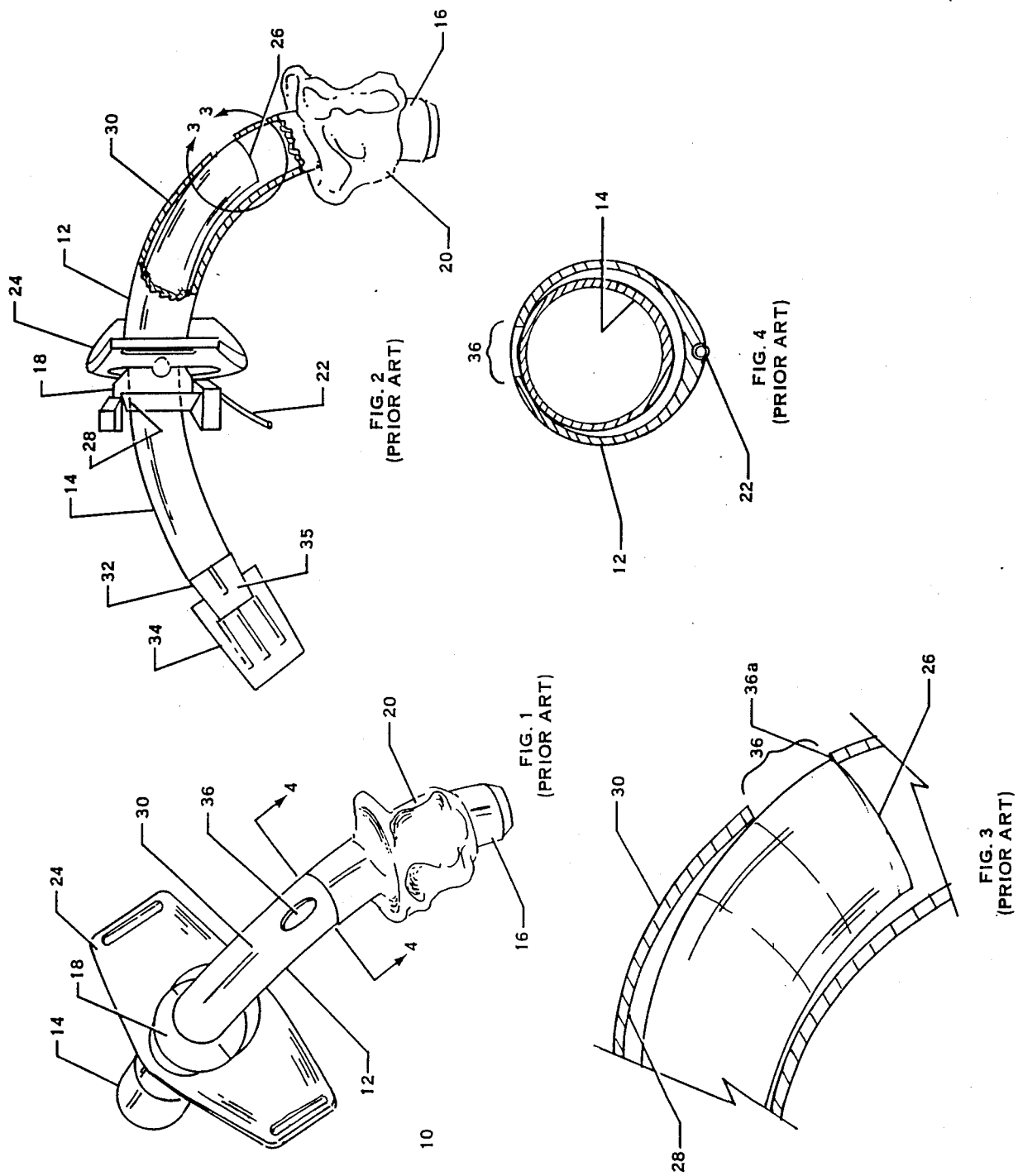

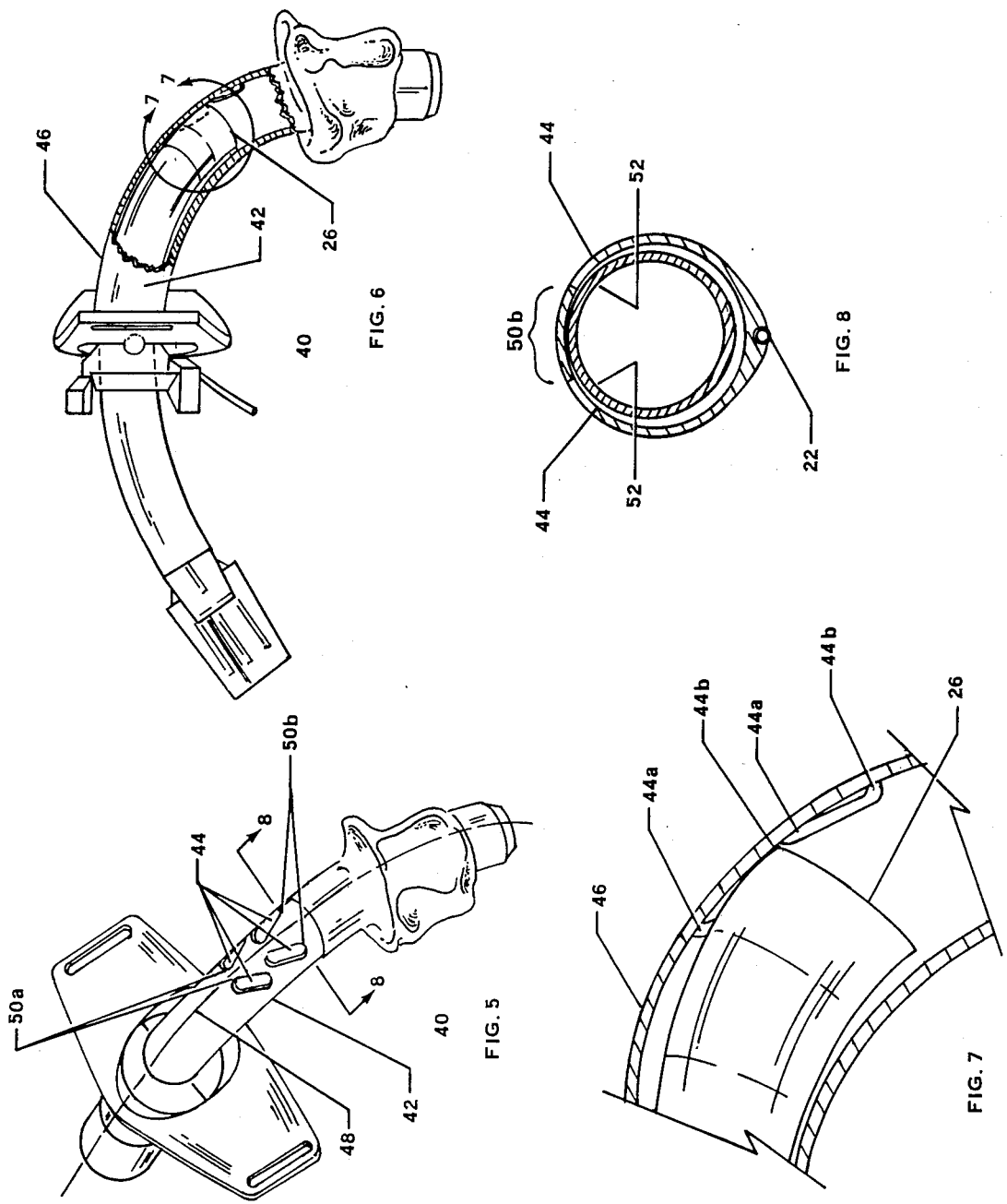

FENESTRATED TRACHEOSTOMY TUBE

BACKGROUND OF THE INVENTION

The present invention relates to a tracheostomy tube particularly a tracheostomy tube having fenestrations in the outer cannula and having a disposable inner cannula.

Tracheostomy tubes have been used for some time to provide a bypass supply of air or mixture of gases to a patient having an obstruction in the larynx or the pharynx area of the throat. The distal end of the tracheostomy tube is inserted into the trachea through an incision in the patient's neck below the obstructed area. The proximal end of the tube remains outside the trachea in communication with ambient air to permit passage of such air into the trachea. The proximal end of the tube can also be attached to a respiratory device to assist the patient's breathing. The distal end also includes an inflatable cuff to seal the distal end of the tube within the throat to further assist the patient's breathing on the respiratory device, as described in U.S. Pat. No. 3,659,612 assigned to the assignee of the present invention. U.S. Pat. No. 3,693,624, also assigned to the assignee of the present invention, discloses a tracheostomy tube having an inner cannula which serves as an inner liner of the outer cannula and can be removed, cleaned and then replaced.

A fenestrated tracheostomy tube is utilized for special applications when a patient is being weaned from the use of the tracheostomy tube. The tube includes fenestrations through the upper surface of the outer cannula in communication with the normal airway of the patient's throat. Periodically, the sealing cuff is deflated, the inner cannula is removed and the outer cannula is plugged, resulting in the patient breathing through the fenestrations and upper airway in a normal manner. This can initially only be done for a short period of time. Then the plug is quickly removed and replaced with the inner cannula, if necessary, to open the tracheostomy airway, then the cuff can be reinflated if periodic ventilation is required. This process is gradually repeated and extended in duration until the patient is able to use the normal upper airway, at which time the tracheostomy tube can be removed.

Current tracheostomy tubes have been developed in which the inner cannula is disposable, as disclosed in U.S. Pat. No. 4,315,505 assigned to the assignee of the present invention. This patent is incorporated herein by reference and particularly discloses an inner cannula constructed from a soft, flexible polymer material such as polyvinyl chloride (PVC) and which can be inexpensibly manufactured using plastic injection molding techniques or can be made from a two-part process including an extrusion step followed by a di-electric end forming step. The disposable inner cannulae are made of thin flexible material which become easily distorted following their manufacture due to their handling, molding characteristics and relaxation of internal stresses; which causes the inner cannula to tend to become oval at the distal tip and tends to increase the radius of curvature. Upon insertion of the somewhat distorted disposable inner cannula into a fenestrated outer cannula, the distal tip of the inner cannula encounters interference or engagement with the fenestration. This problem is particularly apparent where the fenestration is in the form of a generally elliptically or oval shaped opening along the center line of the outer surface (see FIG. 1) as is common in known prior art. The flexible inner cannula which has a generally vertically oriented oval distal tip and has an increased radius of curvature, now upon insertion tends to be forced to slide along the inner surface of the upper wall. The upper portion of the flexible distal tip, therefore generally expands into the oval fenestration resulting in interference when the upper distal tip encounters the vertical rear wall of the fenestration which prevents or delays insertion of the inner cannula into the tube.

The function of the fenestration requires that the opening be generally along the upper surface of the tracheostomy tube. The prior art has incorporated a large oval opening, as previously described which tends to be inadequate due to the interference. The prior art has also incorporated a series of small multiple holes along the outer surface which do not interfere with the inner cannula but tend to become easily clogged and are therefore also considered to be inadequate. The prior art has also utilized a plurality of longitudinal slots spaced away from the center line to reduce such interference; although this is an improvement, the upward air flow is reduced and interference also sometimes occurs and therefore this configuration is also considered to be inadequate.

SUMMARY OF THE INVENTION

It is an object of the present invention to provide a fenestrated tracheostomy tube in which a disposable inner cannula is readily inserted into the outer cannula free from interference with the fenestrations.

It is another object of the present invention to provide a fenestrated tracheostomy tube having fenestrations arranged for maximum upward through-path and which do not interfere with the distal end of an inserted disposable inner cannula.

The present invention solves this problem by providing an improved fenestrated tracheostomy tube which includes a tubular outer cannula which has a distal end for insertion within the trachea and a proximal end which remains outside of the patient. The outer cannula has a generally circular longitudinal radius of curvature and has an upper wall portion with a longitudinal center along its uppermost surface. The tube includes an inner cannula having a distal end and a proximal end which is adapted to fit closely within the outer cannula and to be removably inserted within the outer cannula. The outer cannula has a plurality of slotted fenestrations through the upper wall portion arranged so that the fenestration is slightly spaced from the longitudinal center and forms an acute angle away from the longitudinal center in the direction of the distal end of the outer cannula. Four such fenestrations are preferably arranged with two on each side of the center. With the foregoing fenestration arrangement, the inner cannula is readily inserted into the outer cannula free from interference with the fenestrations.

BRIEF DESCRIPTION OF THE DRAWINGS

While the novel features of the invention are set forth with particularity in the appended claims, the invention will be better understood along with other features thereof from the following detailed description taken in conjunction with the drawings, in which;

FIG. 1 is a front perspective view of a typical fenestrated tracheostomy tube of the prior art;

FIG. 2 is a side elevational view partially in section of the prior art of FIG. 1 showing a disposable inner cannula being inserted into an outer cannula;

FIG. 3 is an enlarged sectional view of area 3—3 of FIG. 2 showing the potential interference of the distal end of the inner cannula with the fenestration;

FIG. 4 is a sectional view taken along line 4—4 of FIG. 1;

FIG. 5 is a front perspective view of the fenestrated tracheostomy tube of the present invention;

FIG. 6 is a side elevational view partially in section of FIG. 5 illustrating the fit of the distal end of the inner cannula with the fenestration of the present invention;

FIG. 7 is an enlarged sectional view of area 7—7 of FIG. 6; and

FIG. 8 is a sectional view taken along line 8—8 of FIG. 5.

DETAILED DESCRIPTION OF THE INVENTION

Referring initially to FIGS. 1 and 2, there is shown a tracheostomy tube 10 of the prior art, including an outer cannula 12, and a removable inner cannula 14 shown partially inserted. The outer cannula 12 is comprised of a tube having a circular longitudinal radius of curvature, a distal end 16 for insertion into the trachea of the patient through an opening in the neck and a proximal end 18 remaining outside the trachea. A typical outer cannula is manufactured from semi-rigid PVC and has a central radius of curvature of about 2.20 inches, an arcuate length of about 86 degrees and an inner diameter of about 0.348 inches. Shown attached to the tracheostomy tube 10 near its distal end 16 is an inflatable cuff 20, which, when inflated, provides an air-tight seal between the tracheostomy tube and the inner wall of the trachea. Such sealing cuffs are described in more detail in U.S. Pat. Nos. 3,659,612 and 3,693,624, assigned to Shiley Inc. The cuff 20 is inflated by means of a flexible inflation line 22 which extends into the cuff 20 from the proximal end 18 along the lower surface of the outer cannula. A swivel neck flange 24 located near the proximal end 18 of the outer cannula is used to secure the tracheostomy tube 10 through the neck of the patient. The inner cannula 14 includes a distal end 26 which is inserted into an internal bore 28 of the outer cannula and which tends to slide along the inner surface of an upper wall portion 30 until fully inserted with a proximal end 32 thereof and secured by a coupling connector 34 having suitable arms 35 which engage the proximal end 18 of the outer cannula.

A typical fenestration 36 of the prior art is illustrated as a generally oval shaped slot along the center of the upper wall portion 30 of the outer cannula 12. As discussed in the background, such a fenestration is utilized to wean a patient away from the use of the tracheostomy tube. To utilize the fenestration 36, the cuff 20 is deflated, the inner cannula 14 is removed and a suitable decannulation plug (not shown) is placed in the proximal end 18 of the outer cannula; which forces the patient to draw air through the fenestration for limited periodic use to gradually increase the patient's upper throat muscles and natural breathing ability. The decannulation plug can be quickly removed and replaced with the inner cannula 14, if necessary, to open the tracheostomy airway, and the cuff 20 can be reinflated if periodic ventilation is required.

As discussed in the background, the inner cannula 14 is typically manufactured to be disposable and is extruded or molded from a very thin, soft, flexible polymer material, preferably a non-toxic PVC having a shore A hardness of about 85. A typical inner cannula has a central radius of curvature of about 2.20 inches (corresponding to that of the outer cannula), an arcuate length of about 86 degrees, an outer diameter of about 0.321 inches and a wall thickness of about 0.030 inches. As a result of cost considerations, the thin material and typical gating and molding techniques, the exact dimensions and configuration of the inner cannula 14 are quite difficult to control, and the distal end tends to become oval in the vertical direction and the radius of curvature tends to increase with time and handling after the inner cannula has been manufactured and inspected. When such a distorted disposable inner cannula 14 is inserted into the bore 28 of the outer cannula, the distal tip 26 tends to be forced to slide along the inner surface of the upper wall portion 30, and the bore tends to contour the configuration of the distal tip to that of the outer cannula. When the distal tip slides over an opening such as the fenestration 36, the upper portion of the distal tip tends to elastically spring into the opening and when the distal tip encounters the proximal facing wall 36a at the distal most end of the slotted opening, an interference results as illustrated particularly in FIGS. 3 and 4. Although the actual engagement which prevents insertion of the inner cannula 14 is relatively rare, even a small percentage represents a severe source of complaint by the patient and represents a significant expense to both the patient and, in scrap, to the manufacturer. In addition, interference during the insertion of the inner cannula gives the patient concern and reflects badly on the perceived quality of the product.

In analyzing the problem, it is noted that the effective performance of the fenestration requires that there be a significant upward through-path between the outer cannula and the throat of the patient suggesting that such fenestrations should be large in area and located at the uppermost surface of the upper wall portion of the outer cannula; while the minimum interference occurs with fenestrations small in area and located at the lowermost portion of the outer cannula. In analyzing solutions to this problem, it was discovered that the least favorable orientation for a fenestration occurred with a lateral slot which readily permits the distal tip of the inner cannula to engage the proximal facing wall of the slot, and that some improvement resulted with a longitudinally oriented slot which was offset or spaced from the center of the upper portion.

Referring now to FIGS. 5 and 6, there is shown an improved fenestrated tracheostomy tube 40 which has an outer cannula 42 that incorporates a uniquely optimized configuration of fenestrations 44. The tube 40 otherwise includes the general structure and features of tube 10 as discussed in references to FIGS. 1–4.

The outer cannula 42 has an upper wall portion 46 having a longitudinal line of center indicated as line 48. The unique orientation on the fenestrations 44 are best illustrated in terms of the line of center 48. The fenestrations 44 are positioned near the center of the arcuate length of the outer cannula (so as to be generally positioned in the center of the trachea of the patient) and can be described as two pairs of slotted fenestrations arranged (in a chevron pattern) having the most proximal ends of each fenestration slightly spaced from the line of center 48, and having each fenestration oriented forming an acute angle away from the longitudinal line of center 48 in the direction of the distal end of the outer cannula (as best illustrated in FIG. 5). It has been determined that an acute angle of about 15 degrees relative to the line of center is quite suitable for the orientation of the fenestrations. However, the orientation permits a wide range of angles, ranging for example from about 5 degrees to about 30 degrees, to be acceptable. This configuration of the fenestrations permits the inner cannula 14 to be readily inserted into the outer cannula 42 free from any interference with the fenestrations and still permits a fully adequate and, what is considered to be, the maximum upward through-path area at the upper wall portion 46, of the outer cannula when the inner cannula is removed.

FIGS. 6-8 illustrate the function of the fenestrations 44. When even a distorted inner cannula is inserted into the bore of the outer cannula 42, the upper portion of the distal tip 26 tends to be forced to slide along the inner surface of the upper wall portion 46, and the bore tends to contour the configuration of the distal tip to that of the outer cannula.

As the distal tip 26 passes over each pair of the fenestrations 44, the upper portion of the distal end tends to elastically spring into the openings. The uppermost portion of the distal end 26 is contoured by a central lateral span 50 between adjacent fenestrations 44, however there are two unsupported arcuate upper portions (illustrated as 52 in FIG. 8) of the distal end 26, which tend to initially extend into the fenestrations.

As the inner cannula 14 is inserted further into outer cannula 42, the central lateral span 50 increases to contour an increasing additional lateral arc of the upper portion of the distal end 26; thereby, the initially oval shaped distal tip tends to become more circular in shape and the amount that each of the two arcuate upper portions 52 extend into the fenestrates is decreased. When the distal end 26 reaches the proximal facing end walls 44b of the fenestrations, the maximum central lateral span 50b (see FIG. 8) has sufficiently contoured the upper portion of the distal end, such that the two arcuate upper portions 52 extend only an insignificant amount, if at all, into the fenestrations and permits the inner cannula to readily pass over the fenestrations free from interference.

The angled slotted fenestrations, in addition to providing the supporting central lateral span 50, also contour the two unsupported arcuate upper portions 52 with a subtle wiping action If pairs of slots were merely longitudinally arranged in parallel having a distance from the line of center 48 equivalent to the maximum span 50b, the unsupported arcuate upper portions 52 would remain at a constant position on the distal end 26 and would tend to have more time in which to further extend into the parallel slots; whereas, the angled relationship of span 50 between the fenestrations 44 constantly shifts the point of the unsupported arcuate upper portions 52, to further facilitate insertion of the inner cannula 14 into outer cannula 42 without interference.

While specific embodiments of the present invention have been illustrated and described herein, it is realized that modifications and changes will occur to those skilled in the art. It is therefore to be understood that the appended claims are intended to cover all such modifications and changes as fall within the true spirit and scope of the invention.

I claim:

1. An improved fenestrated tracheostomy tube for insertion onto a patient's trachea to assist breathing, said tube being adapted to be used with an inner cannula, comprising:
    a tubular outer cannula having a distal end for insertion within the trachea and a proximal end remaining outside;
    said outer cannula having a generally circular cross section and a generally circular radius of curvature and having an upper wall portion thereof with a longitudinal center and a plurality of generally slotted fenestrations; and
    an inner cannula having a distal end and a proximal end and adapted to fit closely and be removably inserted within said outer cannula;
    means for enabling ready insertion of said inner cannula into said outer cannula without interference from said fenestrations, said means including said fenestrations through said upper wall portion of said outer cannula being arranged on both sides of the longitudinal center so that each said fenestration is closely spaced from and forms an acute angle away from the longitudinal center in the direction of the distal end of said outer cannula.

2. The fenestrated tracheostomy tube as in claim 1 wherein said acute angle ranges from 5 degrees to about 30 degrees.

3. The fenestrated tracheostomy tube as in claim 1 comprising four of said fenestrations arranged in adjacent lateral and longitudinal pairs.

4. The fenestrated tracheostomy tube as in claim 3 wherein said acute angle ranges from about 5 degrees to about 30 degrees.

5. The fenestrated tracheostomy tube as in claim 4 wherein said acute angle is about 15 degrees.

* * * * *